(12) United States Patent
Perkins

(10) Patent No.: US 7,433,726 B2
(45) Date of Patent: Oct. 7, 2008

(54) SOC-OX

(76) Inventor: Gene Perkins, 121 S. 1st E. Box 357, Paris, ID (US) 83261

( * ) Notice: Subject to any disclaimer, the term of this patent is extended or adjusted under 35 U.S.C. 154(b) by 152 days.

(21) Appl. No.: 11/238,000

(22) Filed: Sep. 27, 2005

(65) Prior Publication Data

US 2007/0118029 A1 May 24, 2007

Related U.S. Application Data

(60) Provisional application No. 60/613,530, filed on Sep. 27, 2004.

(51) Int. Cl.
*A61B 5/1455* (2006.01)
(52) U.S. Cl. .................. 600/323; 600/340; 600/344
(58) Field of Classification Search ................. 600/323, 600/344, 340
See application file for complete search history.

(56) References Cited

U.S. PATENT DOCUMENTS 5,842,982 A * 12/1998 Mannheimer ............... 600/340
6,470,199 B1 * 10/2002 Kopotic et al. .............. 600/344
6,912,413 B2    6/2005 Rantala et al.
2003/0089136 A1 * 5/2003 Lynch et al. ................. 66/187

* cited by examiner

*Primary Examiner*—Eric F Winakur
*Assistant Examiner*—Etsub D Berhanu
(74) *Attorney, Agent, or Firm*—Raymond M. Galasso; Galasso & Assoc. LP

(57) ABSTRACT

This invention consists of a sock, a sending unit, a receiving unit, a sensor light, and a line that can be connected to a pulse-oximeter cord. A medical professional places the sock over a patient's foot and adjusts its position until the equipment is properly aligned. The cord from the pulse-oximeter can then be attached to the line from the sending unit. The sending unit activates the sensor light that emits radiation at a minimum of two wavelengths. The receiving unit detects the radiation after it passes through the skin and produces an electrical signal in response to the radiation that can be decoded by the pulse-oximeter.

4 Claims, 1 Drawing Sheet

SOC-OX

CROSS REFERENCE TO RELATED APPLICATIONS

This Non-Provisional Patent Application claims priority to U.S. Provisional Application No. 60/613,530 entitled "Soc-Ox" filed on Sep. 27, 2004.

FIELD OF THE DISCLOSURE

The disclosures made herein relate generally to medical devices. The invention discussed herein is in the general classification of pediatric monitoring

BACKGROUND

Traditionally, doctors measure the pulse and oxygen saturation level of a baby's blood with the use of a standard pulse-oximeter. A clamp that is attached to the pulse-oximeter via a cord is placed onto a baby's finger. Pulse measurements are made in the usual manner by showing the number of pulsations as measured through the baby's finger. Oxygen saturation measurements are made by shining light through the baby's skin and measuring the color of the light that is transmitted. Because blood which is being pumped by the heart to the body is red and contains a lot of oxygen and blood returning to the heart is dark red/blue and has less oxygen, the measurements of transmitted light in the form of colors allows the pulse-oximeter to provide an estimate of how much oxygen is in the blood.

Several problems with the finger clamp system exist. Often, it is difficult to keep the clamp on the baby's finger for an extended period of time to obtain meaningful and accurate measurements. The clamp may also be uncomfortable to the baby. Hence, there is a need in the art for a suitable alternative to the finger clamp system that will allow constant and accurate readings without discomfort to the patient.

SUMMARY OF THE DISCLOSURE

The Sox-Ox consists of a specially made sock that connects to a pulse-oximeter and fits comfortably on the patient. The sock has a sending unit, receiving unit, a sensor light, and a line that can be connected to a pulse-oximeter cord.

The principal object of this invention is to provide a device that monitors the pulse and oxygen saturation on infants or pediatric patients.

Another object of this invention is to provide a comfortable and easy to use device for monitoring the pulse and oxygen saturation on infants.

Yet another object this invention is to provide a device that monitors the pulse and oxygen saturation on infants or pediatric patients without causing any discomfort to the patient.

DETAILED DESCRIPTION OF THE DRAWINGS

The Soc-Ox is comprised of at least some of the following: a sock, a sending unit, a receiving unit, a sensor light, and a line that can be connected to a pulse-oximeter cord.

Figure 1:
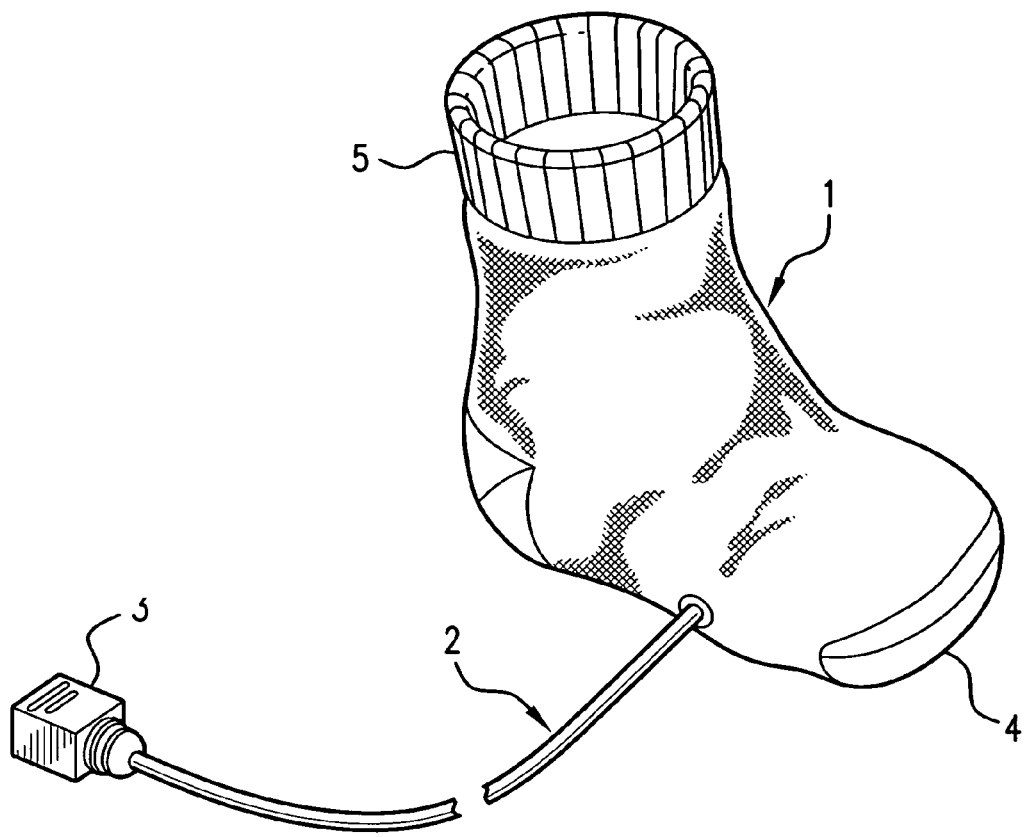
FIG. 1 depicts a perspective view of the preferred embodiment of the invention.

In the preferred embodiment of the invention, shown in FIG. 1, a sock 1 has a line 2 protruding from one side. The line 2 is attached on one end to a sending unit (not pictured) in the toe region 4 of the sock 1 and on the other end has plug 3 that can be connected to a monitor of a pulse-oximeter (not pictured).

On the bottom of the sock 1 and also in the toe region 4, a receiver (not pictured) is attached to the line 2. A sensor light (not pictured) is also located in the middle and top of the toe region 4 of the sock 1. In the ankle region of the sock 1, an elasticized cuff 5 is present to prevent the sock 1 from slipping while it is being worn. It is disclosed herein that, in at least one embodiment, the sock is a cotton and elastic blend sock.

Figure 2:
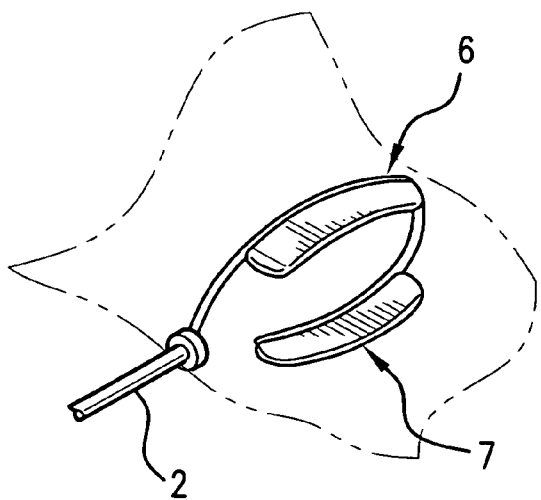
FIG. 2 depicts an interior view of the preferred embodiment of the invention showing the electronic components in the toe region.

In FIG. 2, the sending unit 6 and the receiver 7 that are connected to the line 2 are shown through the toe region of the sock.

A medical professional can slip the sock over a patient's foot and adjust its position until the equipment is properly aligned. The cord from the pulse-oximeter can then be attached to the line from the sending unit. As discussed at length in U.S. Pat. No. 6,912,413, the sending unit activates the sensor light that emits radiation at a minimum of two wavelengths. A receiver detects the radiation after it passes through the skin and produces an electrical signal in response to the radiation that can be decoded by the pulse-oximeter. The electronic components function in the same manner as with the traditional finger clamp pulse-oximeter system. Soc-Ox can remain in place until it provides accurate readings.

All electronic components of the invention will also be ideally selected from those currently having the highest industry ratings. These components will also meet and/or exceed all safety and usage regulations. Wiring and associated connecting hardware should be insulated and otherwise protected from intrusion by any harmful or degrading elements, including water, medium level temperatures, and low to medium impact force.

It should be obvious that the Soc-Ox can come in a variety of sizes and can be used on any patient, including adults.

It will be recognized by those skilled in the art that changes or modifications may be made to the above-described embodiments without departing from the broad inventive concepts of the invention. It should therefore be understood that this invention is not limited to the particular embodiments described herein, but is intended to include all changes and modifications that are within the scope and spirit of the invention as set forth in the claims.

What is claimed is:

1. An oxygen and pulse monitoring device comprising: (a) a signal-carrying line protruding from a sock with a plug that can be connected to a pulse-oximeter, wherein the signal-carrying line includes an exterior portion extending through a first side portion of the sock and an interior portion within the sock, wherein the interior portion of the signal-carrying line laterally extends at least partially around a toe-region of the sock in a manner whereby opposing segments of the signal-carrying line extend laterally in an opposing fashion above and below the toe region and a spanning segment of the signal-carrying line extends along a second side portion of the sock generally opposite the first side portion of the sock to interconnect said opposing segments of the signal-carrying line; (b) a sending unit attached to a first one of said opposing segments of the signal-carrying line and located in the toe region of the sock immediately adjacent to the first one of said opposing segments; (c) a receiving unit attached to a second one of said opposing segments of the signal-carrying line and located in the toe region of the sock immediately adjacent to the second one of said opposing segments; and (d) a sensor light located in the toe region of the sock opposite the receiving unit.

2. The oxygen and pulse monitoring device of claim 1 further comprising an elasticized cuff located on the sock.

3. The oxygen and pulse monitoring device of claim 1 wherein the sock is made of a cotton and elastic blend textile.

4. An oxygen and pulse monitoring device comprising: (a) a signal-carrying line protruding from a cotton and elastic blend sock with a plug that can be connected to a pulse-oximeter, wherein the signal-carrying line includes an exterior portion extending through a first side portion of the cotton and elastic blend sock and an interior portion within the cotton and elastic blend sock, wherein the interior portion of the signal-carrying line laterally extends at least partially around a toe-region of the cotton and elastic blend sock in a manner whereby opposing segments of the signal-carrying line extends laterally in an opposing fashion above and below the toe region and a spanning segment of the signal-carrying line extends along a second side portion of the cotton and elastic blend sock generally opposite the first side portion of the cotton and elastic blend sock to interconnect said opposing segments of the signal-carrying line; (b) a sending unit attached to a first one of said opposing segments of the signal-carrying line and located in the toe region of the cotton and elastic blend sock immediately adjacent to the first one of said opposing segments; (c) a receiving unit attached to a second one of said opposing segments of the signal-carrying line and located in the toe region of the cotton and elastic blend sock immediately adjacent to the second one of said opposing segments; and (d) a sensor light located in the toe region of the cotton and elastic blend sock opposite the receiving unit; and (e) an elasticized cuff located in the ankle region of the cotton and elastic blend sock.

\* \* \* \* \*